(12) United States Patent
Millar et al.

(10) Patent No.: US 6,918,873 B1
(45) Date of Patent: Jul. 19, 2005

(54) INVERTED SENSOR MODULE

(75) Inventors: Huntly D. Millar, Houston, TX (US); Travis H. Bendele, Houston, TX (US); Stephen P. Gray, Houston, TX (US)

(73) Assignee: Millar Instruments, Inc., Houston, TX (US)

( * ) Notice: Subject to any disclaimer, the term of this patent is extended or adjusted under 35 U.S.C. 154(b) by 97 days.

(21) Appl. No.: 10/247,777

(22) Filed: Sep. 19, 2002

(51) Int. Cl.[7] .............................. A61B 5/00; A61B 5/02
(52) U.S. Cl. ................. 600/309; 600/364; 600/365; 600/486; 600/505; 600/547; 600/549
(58) Field of Search ................. 600/309, 310, 600/316, 322, 323, 339, 341, 364, 365, 481, 600/485, 486, 504, 505, 506, 547, 549

(56) References Cited

U.S. PATENT DOCUMENTS

| | | | |
|---|---|---|---|
| 3,906,241 A | * | 9/1975 | Thompson .................. 250/574 |
| 4,825,876 A | * | 5/1989 | Beard ......................... 600/488 |
| 5,058,587 A | * | 10/1991 | Kohno et al. ............... 600/328 |
| 5,411,551 A | * | 5/1995 | Winston et al. ............. 600/347 |
| 5,598,847 A | * | 2/1997 | Renger ....................... 600/504 |
| 5,944,660 A | * | 8/1999 | Kimball et al. ............. 600/310 |
| 6,033,436 A | * | 3/2000 | Steinke et al. ............. 623/1.15 |
| 6,053,873 A | * | 4/2000 | Govari et al. ............... 600/505 |
| 6,115,633 A | * | 9/2000 | Lang et al. .................. 600/547 |
| 6,119,028 A | * | 9/2000 | Schulman et al. .......... 600/345 |
| 6,442,413 B1 | * | 8/2002 | Silver .......................... 600/345 |
| 2002/0183628 A1 | * | 12/2002 | Reich et al. ................. 600/486 |

* cited by examiner

*Primary Examiner*—Eric F. Winakur
(74) *Attorney, Agent, or Firm*—Charles D. Huston; Daffer McDaniel, LLP

(57) ABSTRACT

An inverted sensor module for sensing physical and chemical fluid characteristics in a vessel in a living body. The inverted sensor module includes an inverted sensor bonded to a hollow carrier so that sensing occurs in the lumen of the inverted sensor module. An inverted sensor module comprising one or more inverted sensors is implantable and allows fluid to flow through, thereby allowing for measurements of acute and chronic conditions. The inverted sensor module may be used in series with other inverted sensor modules to assess trends such as pressure gradients along a bloodstream.

30 Claims, 3 Drawing Sheets

INVERTED SENSOR MODULE

RELATED APPLICATION

The current application shares some specification and figures with U.S. patent application Ser. No. 10/247,807, entitled "External Fluid-Filled Catheter Pressure Transducer" filed on Sep. 19, 2002, which is commonly owned or assigned and hereby incorporated by reference.

BACKGROUND OF THE INVENTION

1. Field of the Invention

The present invention relates to a sensor module. More specifically, the present invention relates to an inverted sensor module for use in a fluid vessel in a living body.

2. Related Art

In the medical field, and particularly in the field of medical research, sensors greatly aid in the evaluation of performance and fluid characteristics of vessels in a living body. Sensors are used to determine characteristics such as fluid pressure, temperature, $O_2$, $CO_2$, sugar levels, and/or pH in blood vessels, lymph vessels, ureters, intestines, and chambers of the heart. Medical personnel use this information to evaluate the overall health of a person, and medical researchers use this information to aid in the evaluation of new drugs or procedures.

Typically, sensors are mounted on a catheter for insertion into the vessel. Several patents describe the use of sensors mounted on catheters. However, the use of prior art catheters is not always possible due to the size of the vessel to be monitored in comparison with the catheter. For example, researchers studying cardiac performance in small animals such as mice may encounter blood vessels less than 1 mm in diameter. In these applications, it may not be possible, using prior art sensors, to be able to accurately monitor the cardiac performance directly. In particular, the size of the catheter may be so large that insertion into a blood vessel may block the blood vessel, impair cardiac performance, prevent accurate measurements and cause injury to the subject. It is therefore desirable to provide an improved method and sensor apparatus for detecting and measuring various fluid characteristics in vessels in a living body. It is further desirable to provide a sensor apparatus capable of being used in small vessels.

SUMMARY OF THE INVENTION

The present invention achieves these goals with a unique and advantageous structure for an inverted sensor module that may be used directly inside a living body. The inverted sensor module provides for accurate measurement of fluid characteristics in vessels.

The present invention also provides unique advantages relating to the modularity of the inverted sensor module. Embodiments of the present invention include an inverted sensor device that may be easily inserted into a vessel or bonded to a catheter. In addition, the inverted sensor module may be readily removed and replaced.

In one embodiment, the present invention comprises an inverted sensor module having a sensor operable to provide a signal representative of a physical or chemical characteristic of a fluid in a vessel in a living body. A signal transmission media is coupled to the sensor for transmitting the representative signal. A bonding material is provided for mounting the sensor to the carrier.

In another embodiment, the present invention describes an inverted sensor module with a plurality of inverted sensors mounted thereon. Multiple sensors allow researchers to observe trends in the fluid characteristics along a vessel.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The present invention overcomes the shortcomings of the prior art with an inverted sensor module operable to detect physical and chemical fluid characteristics in small vessels in a living body.

Figure 1A:
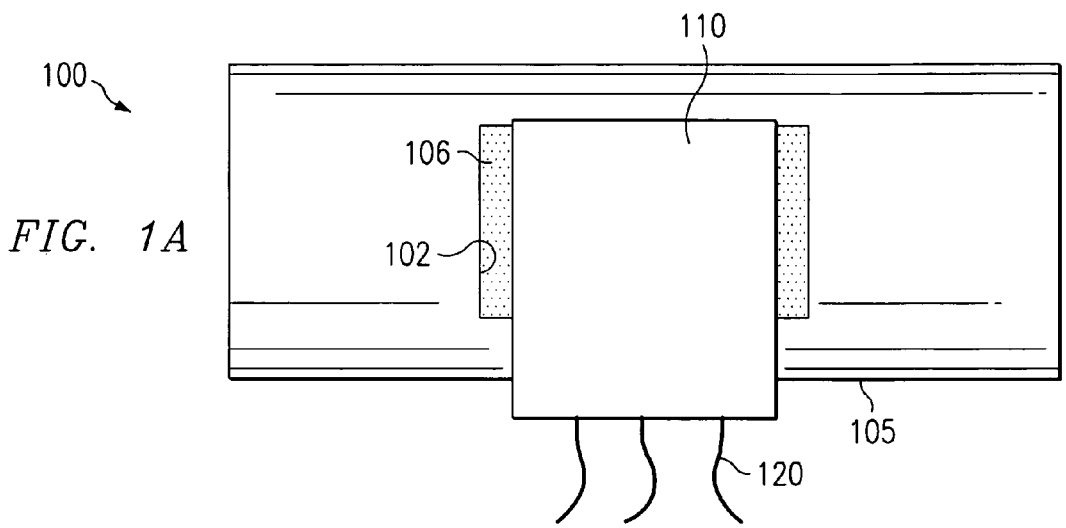
FIG. 1A is a top view of an inverted sensor module according to one embodiment of the present invention.
Figure 1B:
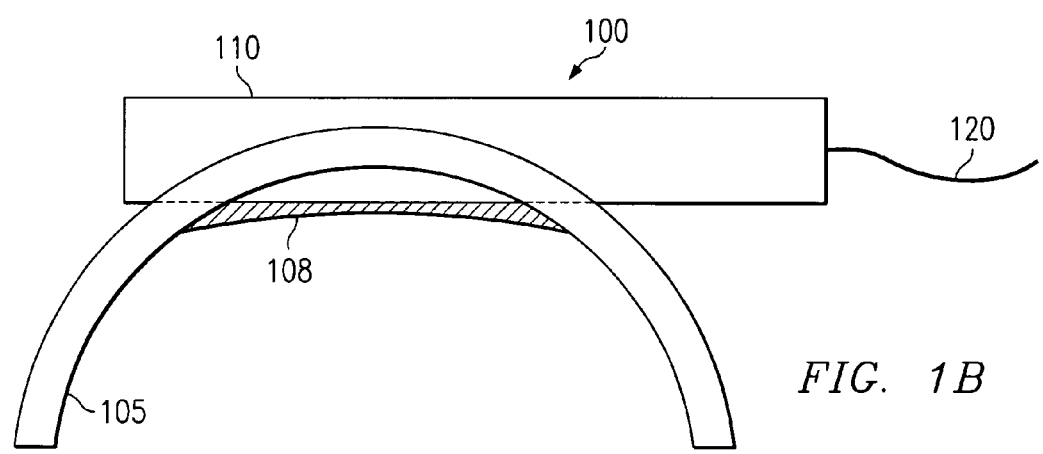
FIG. 1B is an end view of an inverted sensor module according to one embodiment of the present invention.
Figure 1C:
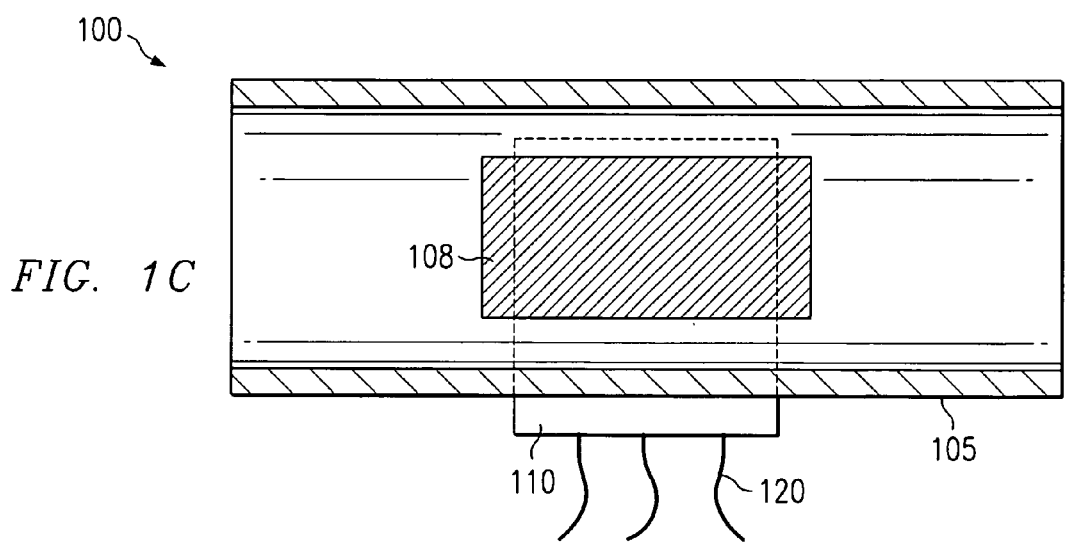
FIG. 1C is a bottom view of an inverted sensor module according to one embodiment of the present invention.

Now referring to the figures, FIGS. 1A, 1B, and 1C are top, end, and bottom views of one embodiment of an inverted sensor module 100 of the present invention. The inverted sensor module 100 comprises a carrier 105 having an inner surface and an outer surface. The carrier 105 is preferably constructed of a high strength biocompatible material such as stainless steel, platinum, titanium or ceramic. The inverted sensor module 100 further comprises a sensor 110, which is inverted such that the sensing side faces the inner surface of the carrier 105. The inverted sensor module 100 further comprises wires or other communication media 120.

The sensor carrier 105 is optimally designed for compatibility with a living body. Although the carrier 105 may have any shape, in a preferred embodiment, the carrier 105 is a convex shape for easier insertion into vessels. The carrier 105 comprises rigid tubing with a known inner cross-sectional area, and maintains the sensor 110 position in close proximity with the fluid being monitored. In some embodiments, the sensor carrier 105 is manufactured from polyimide tubing. An opening 102 such as a window or slot is machined in the carrier 105 such that the sensor 110, which is attached to the carrier 105, detects fluid characteristics on the inside of the carrier 105. Sensor 110 is attached to sensor carrier 105 preferably by bonding material 106. In the preferred embodiment, sensor 110 is bonded to sensor carrier 105 with Room Temperature Vulcanizing (RTV) silicone rubber, although any method of attaching the sensor 110 to the carrier 105 may be used without departing in scope from the present invention. The ends of the carrier 105 can be attached to a vessel in a living body, such as a blood vessel, lymph vessel, ureter, or intestine, for example. Alternatively, the ends of the carrier 105 can be attached to semi-rigid or flexible tubing. Generally, the ends of the carrier 105 are attached to these vessels using any suitable attachment means, such as sutures, clamps, or adhesives.

The sensor 110 detects physical fluid characteristics such as pressure, conductance, and temperature. The sensor 110 may also detect chemical fluid characteristics such as pH, $O_2$, $CO_2$, and blood sugar levels. The type of sensor 110 used may be resistive, capacitive, or semiconductor-based without departing from the scope of the present invention. Sensors 110 may include, but are not limited to, silicon strain gauge sensors, photoelectric, chemical, Doppler, electromagnetic flow profile sensors, and fiber-optic sensors.

The sensor 110 is held in place on the carrier 105 with an appropriate bonding material 106. A preferred material 106 for bonding a sensor 110 to the carrier 105 is RTV silicone rubber (RTV). RTV is a soft, pliant material that does not distort the sensor 110 and provides some electrical isolation of the sensor 110 from the carrier 105.

The communication media 120 provide for communication between the sensor 110 and a monitoring device, as well as power to the sensor 110. Wires or fiber optic lines may be used for communication and power. The communication media 120 may also be part of any standard electrical communication system, such as a Wheatstone bridge. In an alternative embodiment (not shown) communication between sensors 110 and external monitoring devices occur through telemetry.

The inner surface of the inverted sensor module 100 may be coated or lined with an anti-thrombogenic substance 108 to prevent clotting and to provide a clean flow profile (less turbulence) with substantially no bubble traps. Examples of anti-thrombogenic substances include without limitation Parylene® and heparin. The inner surface of the carrier may be alternatively or additionally coated with an anti-infective agent.

Figure 2:
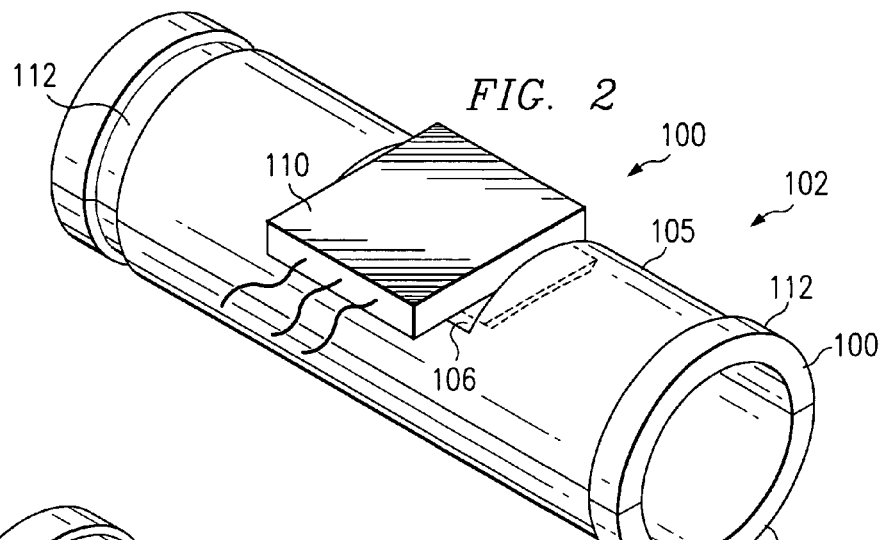
FIG. 2 is a side view of one embodiment of an inverted sensor module bonded to rigid tubing, according to one embodiment of the present invention.

FIG. 2 is an isometric drawing of an inverted sensor module 102 according to one embodiment of the present invention. In this embodiment, the inverted sensor module 100 is bonded to rigid tubing section 101. As a result, inverted sensor module 102 is formed, which generally resembles a tube with a lumen, and inverted sensor module 102 is adapted for monitoring characteristics of fluids flowing through inverted sensor module 102. In a preferred embodiment, the section of tubing 101 and the inverted sensor module carrier 105 are manufactured from the same material, such as polyimide tubing, and are of identical internal diameter to reduce turbulent flow, corrosion, or other effects from using dissimilar materials or varying geometry. Advantageously, the ability to position a sensor to face the concave side or lumen of an inverted sensor module 102 manufactured with tubing of known cross-sectional area and flow-through capabilities allows the sensor 110 to be inserted closer to a source or target, thereby increasing the accuracy of the measurements of the sensor 110.

Additionally, inverted sensor module 102 may also have surface features 112 located at either end for attaching vessels or tubing. Surface features 112 include lips, grooves, knurls, or any other surface feature that may be used in combination with any attachment technique to prevent a vessel from slipping off inverted sensor module 102. Ideally, surface feature 112 is such that any attached vessel is not damaged by the attachment to the feature 112.

Figure 3:
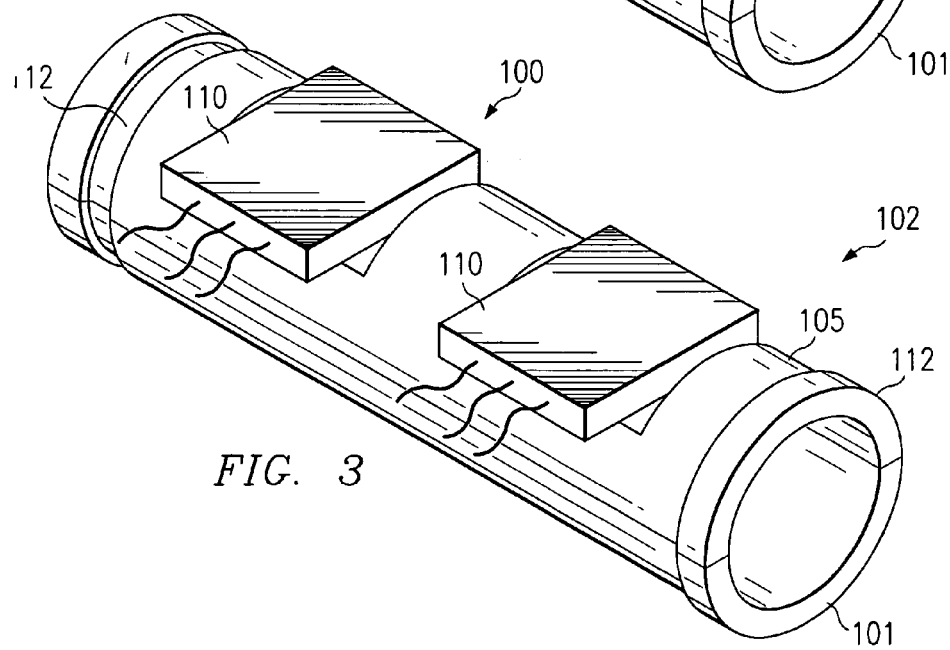
FIG. 3 is an isometric view of an inverted sensor module with multiple sensors, bonded to rigid tubing, according to another embodiment of the present invention.

In FIG. 3, an embodiment of an inverted sensor module 102 having a plurality of pressure sensors 110 is shown. In this embodiment, the sensors 110 are a known distance from each other. Since the cross-sectional area of the inverted sensor module 102 lumen and the distance between the sensors 110 are known, a volumetric flow rate for the vessel may be determined. It will be apparent to those skilled in the art that an accurate assessment of the volumetric flow rate in a vessel may be used to assess or predict performance of the body. It will also be apparent to those skilled in the art that a series of inverted sensor module 102 may used in a vessel at known distances to determine vessel performance.

Figure 4A:
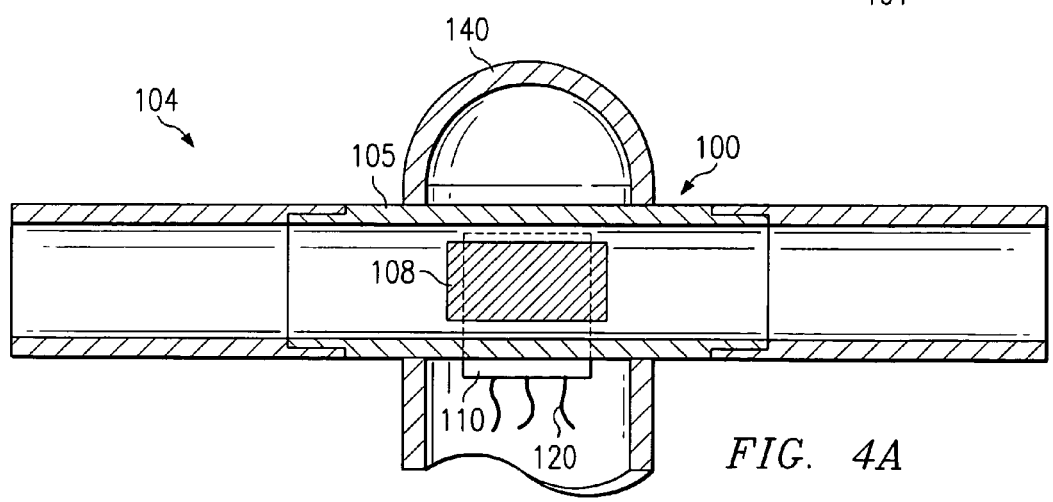
FIGS. 4A and 4B are cross-sectional and isometric views, respectively, of an inverted sensor module with a protective housing, according to one embodiment of the present invention.
Figure 4B:
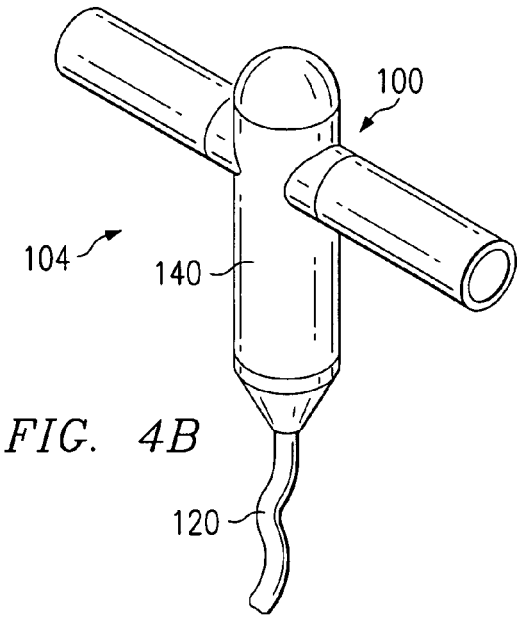

FIGS. 4A and 4B show a cross-sectional side view and an isometric view of an embodiment in which an inverted sensor module 104 is assembled with a protective housing 140 covering inverted sensor module 100. Protective housing 140 may be manufactured from rigid tubing similar to the rigid tubing used to manufacture sensor carrier 105, or housing 140 may be manufactured of other materials. Protective housing 140 helps protect the sensor 110 and the connection to the communication media 120 from damage resulting from use inside a living body. The protective housing 140 may be bonded to the carrier 105 using Room Temperature Vulcanizing (RTV) silicone rubber, a biocompatible epoxy, or any other adhesive, mechanical or thermal technique.

Figure 5:
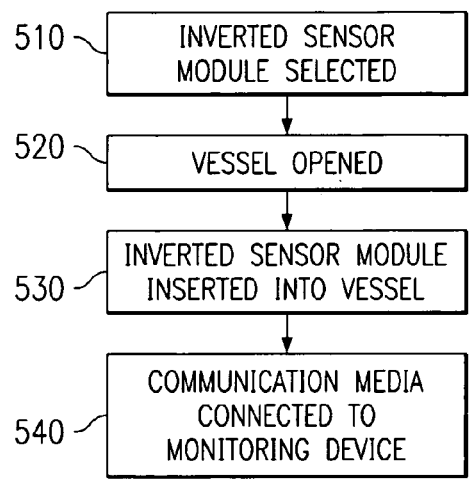
FIG. 5 is a flowchart of steps used to implant an inverted sensor module.

Reference is now made to FIG. 5, which depicts the process flow for using an inverted sensor module 104 as shown in FIGS. 4A and 4B to determine the fluid characteristics within a body vessel. In step 510, an appropriate sized inverted sensor module 104 is selected based on the size of the vessel to be monitored. Inverted sensor module 104 of different lumen diameters, carrier lengths, or overall sizes give medical personnel and researchers the ability to take measurements of more characteristics, closer to a target region, on different size vessels, and with less impact on the surrounding body tissues. Additionally, this minimizes the negative physiological effects of monitoring a vessel, such as the disruption of blood circulation. By minimizing the negative physiological effects, trauma may be reduced, recovery may be quicker, and an inverted sensor module 104 may be left in the body for longer periods of time, allowing monitoring of both acute and chronic conditions.

In step 520, the vessel is opened for insertion of an inverted sensor module 104. For purposes of this disclosure, opening the vessel generally means the vessel may be cut all the way through or the vessel may be scored. For purposes of this disclosure, scoring a vessel means generally that an opening, such as a slit, is made in the vessel. The choice of whether to cut or score a vessel may be based on the particular application, size of the inverted sensor module 104, size of the vessel, health of the living body being monitored, type of vessel being monitored, fluid characteristic being monitored, or any other parameter, without departing in scope from the present invention.

In step 530, the inverted sensor module 104 is inserted into the vessel and the vessel is closed or sealed around the inverted sensor module 104. In situations in which the vessel is cut all the way through, the ends of the cut vessel are attached to the ends of the inverted sensor module 104 so that all fluid moving through the vessel must pass through the inverted sensor module 104. The ends may be attached with sutures, adhesives, clamps, or any other technique that ensures all fluid travels through the inverted sensor module 104 and that has little negative physiological effect on the vessel. In situations in which the vessel is scored, the inverted sensor module 104 is inserted into the vessel and the vessel is then sutured or sealed around the inverted sensor module 104 so that all fluid moving through the vessel must pass through the inverted sensor module 104.

In step 540, the communication medium 120 is connected to a monitoring device and measurements of the fluid characteristics may be taken.

Once the inverted sensor module 104 is inserted in the vessel and the vessel is attached to the ends of the inverted sensor module 104 or closed around the inverted sensor module 104, the living body may then be closed so that only the communication medium 120 protrudes from the body. In this manner, long-term monitoring may occur.

Figure 6:
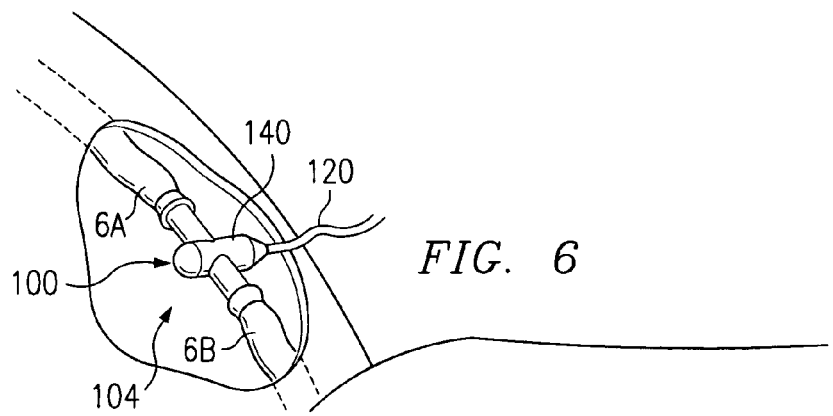
FIG. 6 is a drawing of one embodiment of an inverted sensor module implanted in a human body.

FIG. 6 is an illustration of an inverted sensor module 104, according to the preferred embodiment of the invention, implanted in an artery in a living body. As shown, a vessel is cut and the ends, 6A and 6B, are attached to the ends of inverted sensor module 104 such that all fluid flowing through the vessel must pass through inverted sensor module 104. As discussed above, the present invention is not limited for use in an artery, but may be used in intestines, ureters, lymph vessels, veins, chambers of the heart, or any other type of fluid vessel without departing in scope from the present invention.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as exemplary embodiments. Various changes may be made in the shape, size, and arrangement of parts. For example, equivalent elements or materials may be substitute for those illustrated and described herein, and certain features of the invention may be utilized independently of the use of other features, all as would be apparent to one skilled in the art after having the benefit of this description of the invention.

What is claimed is:

1. An inverted sensor module for sensing one or more characteristics of fluid in one or more vessels in a living body, the inverted sensor module comprising;
   a sensor carrier having one or more openings, wherein said sensor carrier is sized for insertion within said one or more vessels, and wherein an inner surface of said sensor carrier is coated or lined with a substance for reducing turbulence of the fluid flowing through a lumen of said sensor carrier;
   one or more sensors mounted to said sensor carrier, such that a sensing side of said one or more sensors is exposed to the inside of said sensor carrier through said one or more openings;
   a surface feature formed on each end of said inverted sensor module, such that the ends of a cut vessel may be attached to both ends of said inverted sensor module; and
   communication media operatively connected to said one or more sensors, said communication media operable for communicating sensor information to a monitoring device.

2. The inverted sensor module of claim 1, wherein said one or more sensors sense one or more physical characteristics of said fluid.

3. The inverted sensor module of claim 2, wherein said one or more characteristics comprises flow velocity.

4. The inverted sensor module of claim 2, wherein said one or more characteristics comprises pressure.

5. The inverted sensor module of claim 2, wherein said one or more characteristics comprises temperature.

6. The inverted sensor module of claim 2, wherein said one or more characteristics comprises conductance.

7. The inverted sensor module of claim 1, wherein said one or more sensors sense one or more chemical characteristics of said fluid.

8. The inverted sensor module of claim 7, wherein said one or more characteristics comprises pH.

9. The inverted sensor module of claim 7, wherein said one or more characteristics comprises $O_2$ concentration.

10. The inverted sensor module of claim 7, wherein said one or more characteristics comprises $CO_2$ concentration.

11. The inverted sensor module of claim 7, wherein said one or more characteristics comprises glucose concentration.

12. The inverted sensor module of claim 1, wherein the communication media are coupled to the one or more sensors with wires, fiber optics, or telemetry.

13. The inverted sensor module of claim 1, further comprising a portion of tubing bonded to said inverted sensor module such that fluids may flow through said inverted sensor module, wherein said inverted sensor module is operable to detect the one or more characteristics of the fluid flowing through said inverted sensor module.

14. The inverted sensor module of claim 13, wherein said surface feature on each end of said inverted sensor module comprises a groove.

15. The inverted sensor module of claim 13, wherein said surface feature on each end of said inverted sensor module comprises a lip.

16. The inverted sensor module of claim 13, wherein said surface feature on each end of said inverted sensor module comprises a knurl.

17. The inverted sensor module of claim 13, wherein said surface feature on each end of said inverted sensor module comprises a chemical etch.

18. The inverted sensor module of claim 13, further comprising a protective housing for said sensor.

19. The inverted sensor module of claim 13, wherein said one or more vessels in said living body comprise blood vessels, lymph vessels, ureters, intestines or chambers of the heart.

20. The inverted sensor module of claim 1, wherein said substance comprises an antithrombogenic substance, which is applied to the inner surface of the sensor carrier to reduce blood clotting within the sensor carrier and to produce a completely smooth surface.

21. The inverted sensor module of claim 1, wherein said substance comprises an anti-infective agent, which is applied to the inner surface of the sensor carrier to reduce a possibility for infection and to produce a completely smooth surface.

22. The inverted sensor module of claim 1, wherein said sensor carrier is formed from a rigid biocompatible material selected from stainless steel, platinum, titanium, ceramic and a rigid polymer-based tubing.

23. The inverted sensor module of claim 22, wherein said one or more sensors are mounted to said sensor carrier with a plant bonding material that provides at least some electrical isolation from said sensor carrier.

24. A method for determining fluid characteristics in a living body using an inverted sensor module, comprising the steps of:

opening a fluid vessel in the living body, wherein said vessel is scored or cut;

inserting an inverted sensor module, comprising one or more sensors, into said vessel; and closing said vessel such that all fluid flow through said vessel passes through said inverted sensor module, wherein said closing comprises connecting cut surfaces of the vessel to surface features formed at opposing ends of said inverted sensor module, and wherein said inverted sensor module is operable to sense fluid characteristics and send information about said fluid characteristics to a monitoring device outside the living body.

25. The method of claim 24, further comprising the step of operably connecting said one or more inverted sensor modules via one or more communication media to a monitoring device located outside the living body.

26. A method for manufacturing an inverted sensor module configured for insertion within a living body, wherein the method comprises the steps of:

machining one or more openings into a sensor carrier;

bonding one or more sensors into said one or more openings machined into said sensor carrier such that a sensing side of said one or more sensors is exposed toward a concave side of said sensor carrier; and creating a surface feature of an end of said inverted sensor module such that a vessel located within the living body may be connected to said inverted sensor module.

27. The method of claim 26, further comprising the steps of:

applying an antithrombogenic substance to said sensing side of said one or more sensors; and connecting communication media to said sensor.

28. The method of claim 26, further comprising the step of bonding a portion of tubing to said inverted sensor module, such that fluids may flow through a lumen of said inverted sensor module.

29. The method of claim 28, further comprising the step of creating a surface feature on an end of said inverted sensor module such that tubing may be connected to said inverted sensor module.

30. The method of claim 28, further comprising the step of bonding a protective housing to said inverted sensor module.

* * * * *

UNITED STATES PATENT AND TRADEMARK OFFICE
CERTIFICATE OF CORRECTION

PATENT NO.   : 6,918,873B1
DATED        : September 19, 2002
INVENTOR(S)  : Millar et al.

It is certified that error appears in the above-identified patent and that said Letters Patent is hereby corrected as shown below:

Column 6,
Line 59, after "selected from", insert -- the group consisting of --.
Line 63, delete "plant" and subsititute -- pliant --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,918,873 B1 Page 1 of 1
DATED : July 19, 2005
INVENTOR(S) : Millar et al.

It is certified that error appears in the above-identified patent and that said Letters Patent is hereby corrected as shown below:

<u>Column 6,</u>
Line 59, after "selected from", insert -- the group consisting of --.
Line 63, delete "plant" and substitute -- pliant --.

This certificate supersedes Certificate of Correction issued March 7, 2006.

Signed and Sealed this

Eleventh Day of April, 2006

JON W. DUDAS
*Director of the United States Patent and Trademark Office*